US00PP17082P3

(12) United States Plant Patent
Schmulling

(10) Patent No.: US PP17,082 P3
(45) Date of Patent: Sep. 5, 2006

(54) ***SUTERA* PLANT NAMED 'BLISCH'**

(50) Latin Name: *Sutera cordata*
Varietal Denomination: Blisch

(76) Inventor: Wihelm Schmulling, Temming 83, 48727, Billberbeck (DE)

( * ) Notice: Subject to any disclaimer, the term of this patent is extended or adjusted under 35 U.S.C. 154(b) by 0 days.

(21) Appl. No.: 10/840,458

(22) Filed: May 5, 2004

(65) Prior Publication Data

US 2005/0132454 P1 Jun. 16, 2005

Related U.S. Application Data

(63) Continuation-in-part of application No. 10/734,559, filed on Dec. 12, 2003.

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

| | | | |
|---|---|---|---|
| PP10,966 | P | 6/1999 | Rother |
| PP11,835 | P2 | 4/2001 | Rother |
| PP14,191 | P2 | 9/2003 | Westhoff |

OTHER PUBLICATIONS

GTITM UPOV ROM Citation for 'Blisch' as per QZ PBR 011100; Jul. 2, 2001.*

A copy of U.S. Appl. No. 10/734,559, filed Dec. 12, 2003.

A copy of Plant Breeders' Rights Application filed in Canada for 'Blisch'.

A copy of Plant Breeders' Rights Application filed in the European Union for 'Blisch'.

* cited by examiner

*Primary Examiner*—Kent Bell
(74) *Attorney, Agent, or Firm*—Wood, Phillips, Katz, Clark & Mortimer

(57) ABSTRACT

A new and distinct *Sutera* plant named 'Blisch' characterized by its large white-colored flowers, dark green-colored foliage and a spreading and trailing growth habit.

1 Drawing Sheet

Latin name of the genus and species of plant claimed: *Sutera cordata.*
Variety denomination. 'Blisch'.

BACKGROUND OF THE INVENTION

The present invention relates to a new and distinct cultivar of *Sutera* plant botanically known as *Sutera cordata* and hereinafter referred to by the cultivar name 'Blisch'.

The new cultivar originated in a controlled breeding program during the summer of 2000 at Billerbeck, Germany. The progeny of this breeding were evaluated in the summer of 2001 and one plant among that progeny was selected and eventually named 'Blisch'. The objective of the breeding program was the development of *Sutera* cultivars with a trailing habit and large flowers.

The identity of the female (seed) parent of the new cultivar used in the above-described breeding program by the inventor is not known. The identity of the male (pollen) parent of the new cultivar used in the above-described breeding program by the inventor is not known.

Asexual reproduction of the new cultivar by terminal stem cuttings taken since 2001 in West Chicago, Ill., has demonstrated that the new cultivar reproduces true to type with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

It was repeatedly found that the cultivar of the present invention:

1. Exhibits large white-colored flowers,
2. Forms dark green-colored foliage, and
3. Exhibits a spreading and trailing growth habit.

Of the many *Sutera* cultivars known to the inventor, the most similar to the new cultivar is 'Novasnow' (U.S. Plant Pat. No. 12,026). However, in a side-by-side comparison, conducted at West Chicago, Ill., plants of the new cultivar differed from plants of 'Novasnow' in the following characteristics:

1. Plants of the new cultivar had smaller leaves than plants of 'Novasnow', and
2. Plants of the new cultivar had a larger area of spread than plants of 'Novasnow'.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from the color values cited in the detailed description, which accurately describes the colors of 'Blisch'. The plants were grown in 10 cm pots for 9 weeks in a greenhouse at West Chicago, Ill.

DETAILED BOTANICAL DESCRIPTION

Figure 1:
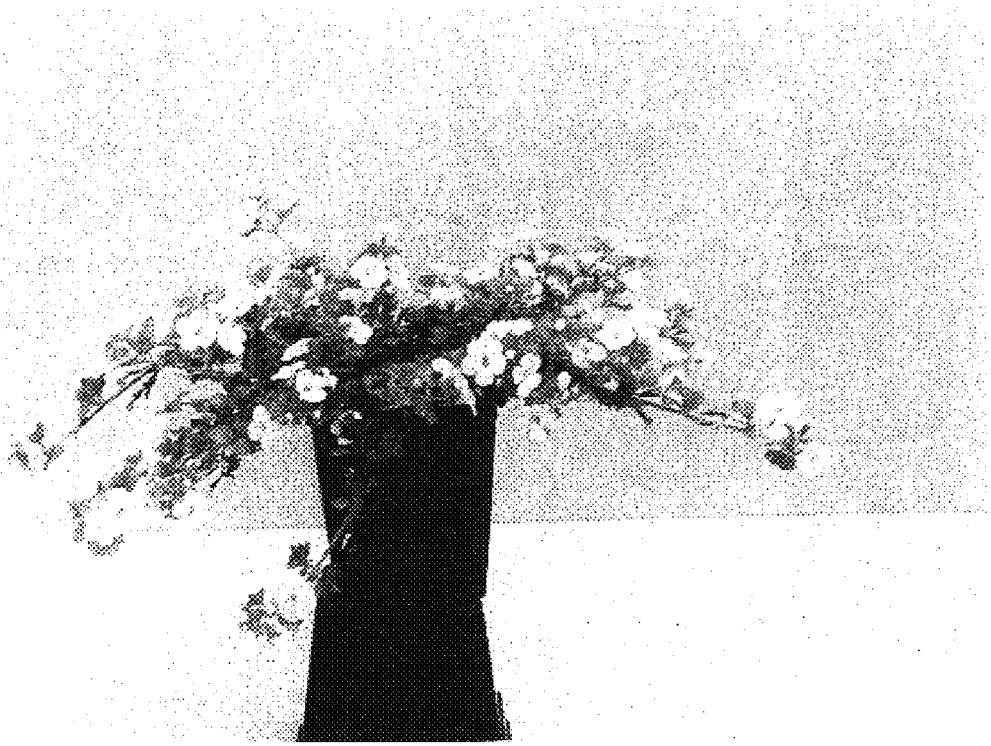
FIG. 1 illustrates a side view of the overall growth and flowering habit of 'Blisch'.
Figure 2:
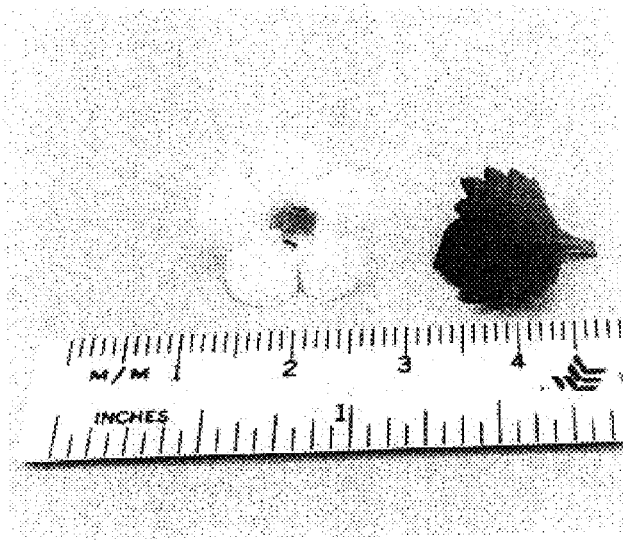
FIG. 2 illustrates a close-up view of an individual leaf and flower of 'Blisch'.

The chart used in the identification of colors described herein is The R.H.S. Colour Chart of The Royal Horticultural Society, London, England, 1995 edition, except where color terms of ordinary significance are used. The color values were determined on Jul. 14, 2003, between 10:30 and 11:30 a.m. under natural daylight conditions.

The following descriptions and measurements describe plants produced from cuttings taken from stock plants and grown in a double polycarbonate-covered greenhouse under conditions comparable to those used in commercial practice. Plants were grown in 10 cm pots for 9 weeks, while utilizing a soilless growth medium. Greenhouse temperatures were maintained at approximately 65–75° F. during the day and approximately 55–60° F. during the night. Greenhouse light levels were maintained at approximately 4,000–8,000 foot-candles during the day.

Botanical classification: *Sutera cordata,* cultivar 'Blisch'.

Parentage:

*Female parent.*—Is unknown.

*Male parent.*—Is unknown.

Propagation:

*Type cutting.*—Terminal stem.

*Time to initiate roots.*—Approximately 7 to 10 days.

*Time to produce a rooted cutting.*—Approximately 21 to 28 days.

*Root description.*—Fibrous.

*Rooting habit.*—Freely branching.

Plant description:

*Crop time.*—Approximately 5–7 weeks from planting of a rooted cutting.

*Growth habit.*—Moderately vigorous with good basal branching. Pinching improves basal branching.

*Form.*—Spreading and trailing.

*Size.*—A mature plant, 9 weeks after the planting of a rooted cutting, commonly measures approximately 9 cm in height from soil level to top of plant plane and approximately 48.2 cm in diameter (plant spread).

*Branch description.*—Quantity: Approximately 6 main branches with lateral branches at every node. Strength: Strong. Length of main branches: Approximately 26 cm. Diameter of main branches: Approximately 2 mm. Length of lateral branches: Approximately 16 cm. Diameter of lateral branches: 1.8 mm. Texture of all branches: Densely pubescent with short soft hairs. Color of all branches: 144A. Internode length at middle of main branch is approximately 2.8 cm.

*Foliage.*—Quantity: Approximately 30 per main branch. Fragrance: Pungent. Form: Simple. Arrangement: Opposite. Aspect: At an acute angle to the stem. Shape: Ovate. Margin: Dentate. Apex: Broadly acute. Base: Truncate. Venation pattern: Pinnate. Leaf length: Approximately 1.3 cm. Leaf width: Approximately 1.4 cm. Texture of upper surface: Puberulent. Texture of lower surface: Glabrous with dense pubescence along veins. Color of upper surface of both young and mature foliage: 137A with venation of 143B. Color of lower surface of both young and mature foliage: 137C with venation of 143B. Petiole length: Approximately 3.3 mm. Petiole diameter: Approximately 1 mm. Petiole texture: Densely pubescent. Petiole color: Closest to 143B.

Flowering description:

*Flowering habit.*—Freely flowering under outdoor growing conditions with substantially continuous blooming from spring through fall, and year round in greenhouse environment.

Flower description:

*Type.*—Solitary, axillary and salverform. Flowers are persistent and non fragrant.

*Bud.*—Shape: Globular. Length: Approximately 6.3 mm. Diameter: Approximately 4.3 mm. Color: 155D.

*Corolla.*—Shape: Round. Diameter: Approximately 1.7 cm. Corolla is composed of five rectangular shaped petals fused at the base forming a tube. Petals are iridescent. Petal length from the tube opening: Approximately 5 mm. Petal width: Approximately 3 mm. Petal margin: Entire. Apex: Flat to somewhat emarginated. Petal texture: Glabrous. Color of upper surface of petals when flower is opening and when fully opened is closest to 155D. Color at base of petals, around tube opening, and into the tube: 151C. Color of lower surface of petals both when opening and when fully opened: Closest to 155D. Corolla tube: Length: Approximately 1.2 cm. Diameter: Approximately 2 mm. Texture: Pubescent on both inner and outer surface. Color of both inner and outer surface: 154D. Color of tube venation: 12A. Corolla depth: Approximately 2 mm.

*Calyx.*—Formed by five sepals, fused at base to form tube. Sepal shape: Linear. Sepal width: 0.07 mm. Sepal apex: Acute. Sepal margin: Entire. Texture: Both surfaces: Densely pubescent. Color of both surfaces: 138A. Calyx length: Approximately 3 mm. Diameter at apex: Approximately 4 mm. Diameter at base: Approximately 2 mm.

*Peduncle.*—Moderately strong. Texture: Densely pubescent. Aspect: At an acute angle to the stem. Length: Approximately 7 mm. Diameter: 1 mm. Color: 144B.

*Reproductive organs.*—Androecium: There are 4 stamens fused to the inside of the corolla tube, 2 above and 2 below the stigma. Anther length: Approximately 1 mm. Anther color: 7B. Pollen amount: Abundant. Pollen color: 13B. Gynoecium: Pistil quantity: One. Pistil length: Approximately 9 mm. Stigma length: Approximately 1 mm. Stigma color: 144C. Style length: Approximately 6 mm. Style color: N144C. Ovary diameter: Approximately 2 mm. Ovary color: 144C.

Seed and fruit production: Neither seed nor fruit production has been observed.

Disease and pest resistance: Resistance to pathogens and pests common to *Sutera* has not been observed.

What is claimed is:

1. A new and distinct cultivar of *Sutera cordata* named 'Blisch' substantially as herein shown and described.

* * * * *